United States Patent [19]

Ford

[11] 4,280,624
[45] Jul. 28, 1981

[54] BOTTLE INSPECTION APPARATUS

[75] Inventor: Geoffrey E. Ford, Bedford, England

[73] Assignee: TI Fords Limited, Bedford, England

[21] Appl. No.: 947,547

[22] Filed: Oct. 2, 1978

[30] Foreign Application Priority Data

Oct. 13, 1977 [GB] United Kingdom ............... 42553/77

[51] Int. Cl.³ .............................................. B07C 5/342
[52] U.S. Cl. .................................. 209/524; 209/585;
209/934; 209/939; 250/223 B; 356/240
[58] Field of Search ............... 209/524, 526, 585, 934,
209/939; 250/223 B; 356/240; 198/576, 577

[56] References Cited

U.S. PATENT DOCUMENTS

| 3,746,784 | 7/1973 | Van Oosterhout | 250/223 B |
|---|---|---|---|
| 3,894,806 | 7/1975 | Remy et al. | 209/524 X |
| 3,908,815 | 9/1975 | Carter | 198/577 X |
| 3,923,158 | 12/1975 | Fornåå | 209/526 |
| 3,932,042 | 1/1976 | Faani et al. | 209/524 X |
| 4,002,823 | 1/1977 | Van Oosterhout | 250/223 B |
| 4,025,201 | 5/1977 | Deane | 209/526 X |

FOREIGN PATENT DOCUMENTS 2834587 3/1979 Fed. Rep. of Germany ........... 356/240

Primary Examiner—Joseph J. Rolla
Attorney, Agent, or Firm—Brisebois & Kruger

[57] ABSTRACT

The invention relates to an apparatus for inspecting the side walls of transparent bottles for the detection of dirt or foreign bodies therein which eliminates the necessity of rotating the bottle during inspection. The inspection is effected by projecting a plurality of images of the side walls of a bottle, as viewed from at least two different directions in plan, on to at least one integrated circuit device comprising an array of photodiodes arranged in a plurality of rows in combination with means to interrogate each diode in turn, along each row in turn, to provide a video signal comprising a sequence of electrical signals corresponding to the light energy each diode has received. The video signal is differentiated and unwanted signals outside of the limits of the side walls to be inspected are gated out, whereby to generate a video output pulse representative of dirt in the bottle.

7 Claims, 7 Drawing Figures

BOTTLE INSPECTION APPARATUS

FIELD OF THE INVENTION

The present invention relates to apparatus, herein referred to as bottle inspection apparatus, for the detection of dirt or foreign bodies in transparent bottles or other containers (herein referred to as "bottles") before they are filled and offered for sale, paricularly in bottles such as milk or beer bottles which are re-used after washing. The inspection apparatus may detect dirt or foreign bodies lying in the base area of empty bottles, so-called "base inspection." However, many foreign bodies, such as mould growths, cement or paint splashes which can adhere to the sides of a bottle, are not detected by base inspection and can only be detected by inspecting the side walls of the bottles, so-called "side inspection." The present invention more particularly relates to apparatus for the side inspection of bottles.

PRIOR ART

Many attempts have been made to devise a machine which will inspect the sides of the bottle. British Pat. No. 1,098,174 and also British Pat. No. 1,430,547 both describe machines which inspect the sides of the bottle.

In both machines, and in other side-inspection machines which have been marketed, bottles have to be transferred off the normal bottle conveyor by a star wheel and placed on a multistation revolving turret where the inspection takes place, and then transferred back to the bottle conveyor by a star wheel. Furthermore, each bottle has to be rotated on its axis by some means during the actual inspection process to ensure that its whole circumference is scanned.

Such mechanism to rotate the bottle is vulnerable to damage or jamming if a broken bottle or glass fragments enter the machine, and since this mechanism has to be provided for each of the stations of the turret, frequently ten stations, the cost is very considerable. It is also difficult to devise a rotation mechanism which will accommodate the inevitable dimensional variations present in a typical population of bottles, such as height variations, body ovality and non-vertical bottle axes. Furthermore, the star wheel transfer mechanism and the necessity to rotate the bottles during inspection has limited the inspection speeds of these machines to about 400 bottles per minute, which is insufficient to meet the requirements of modern high speed bottling lines running at speeds in excess of 750 bottles per minute.

SUMMARY OF THE INVENTION

The present invention has for its object to overcome these disadvantages and to provide a bottle inspection apparatus which is capable of inspecting the side walls of a bottle without requiring its rotation and at speeds of 750 bottles per minute or more.

The invention consists in apparatus for inspecting the side walls of a transparent or translucent bottles for the detection of dirt or foreign bodies, wherein a plurality of images of the side walls of a bottle to be inspected, as viewed from at least two different directions (in plan view), are projected on to at least one integrated circuit device comprising an array of photo-diodes arranged in a plurality of rows in combination with means to interrogate each diode in turn, along each row in turn, to provide a video signal comprising a sequence of electrical signals corresponding to the light energy each diode has received, and wherein the video signal is differentiated and means are provided for gating-out unwanted signals outside the limits of the side walls of the bottle to be inspected whereby to generate a differentiated video output pulse representative of dirt or foreign bodies in the bottle.

It has been found possible to see contaminating objects anywhere on the inside surface of the side walls of a bottle by side inspection from two directions at right angles, in plan view. Both the near and far side walls of the bottle can be seen from each of the two viewing directions. However, if desired, the side inspection may be carried out from more than two directions, in plan view.

A feature of the invention consists in the mechanism for feeding the bottles through the inspection station whereby the bottles, arriving in substantially touching relationship on the normal bottle line conveyor, are accelerated to that they are spaced apart when subject to the side inspection and they may then decelerated to the normal bottle line conveyor speed to be returned to said conveyor in substantially touching relationship whereby to facilitate selective rejection of any bottle which the inspection has detected as being dirty or to contain a foreign body.

BRIEF DESCRIPTION OF THE DRAWINGS

In order that the invention may be more clearly understood, reference will now be made to the accompanying drawings, in which:

FIG. 1a shows a modification.

DETAILED DESCRIPTION OF THE INVENTION

Figure 1:
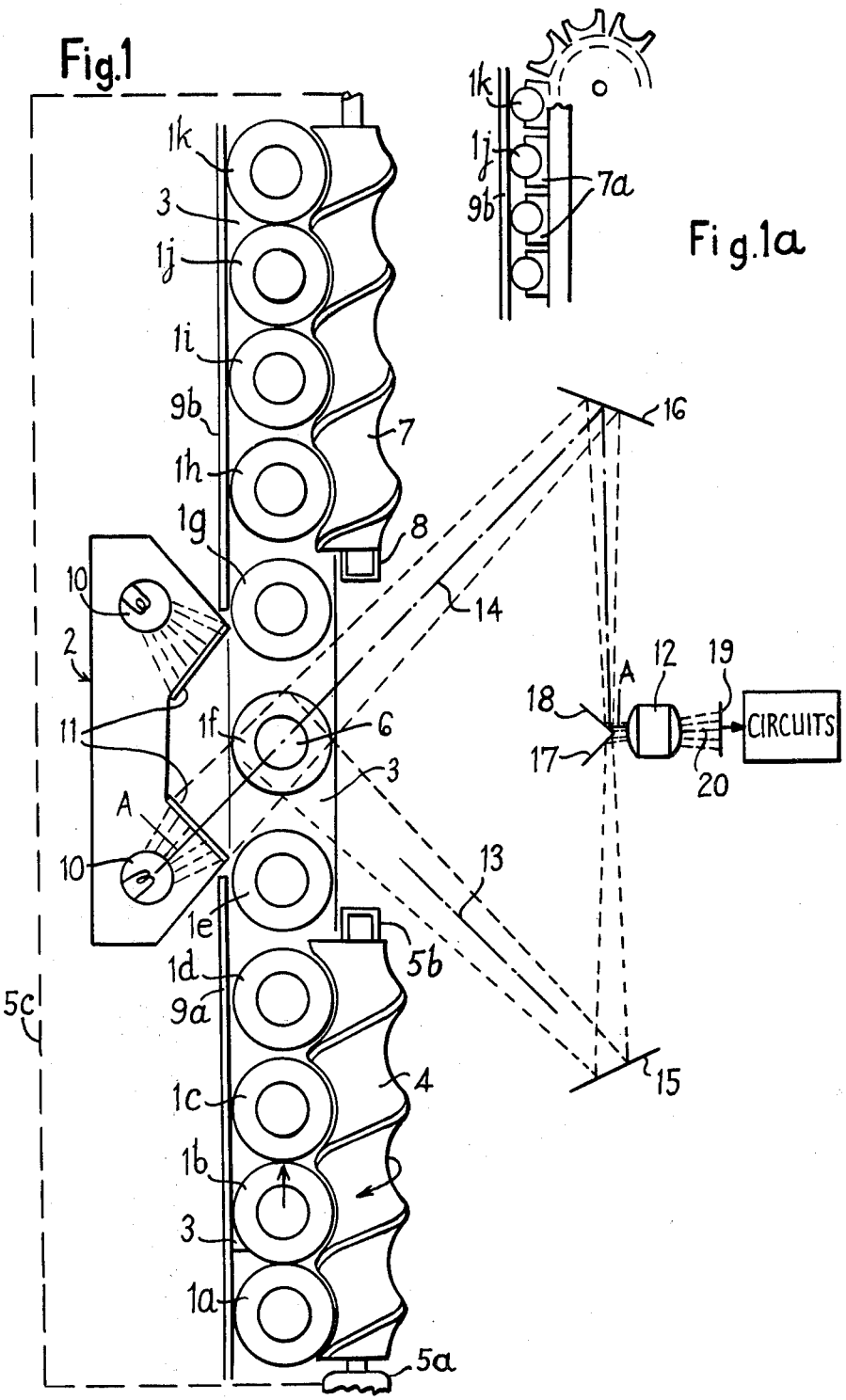
FIG. 1 is a schematic plan view of a bottle inspection machine incorporating the present invention.

FIG. 1 shows a general plan view of the machine with bottles 1a, 1b . . . 1k passing through the inspection station 2 in a straight line in the direction of the arrow, supported underneath by a moving conveyor 3.

A helical feed screw 4 is provided at the input end of the machine and is rotated by a motor and variable speed drive 5a at a rate appropriate for the number of bottles per minute being handled on the main bottle-line conveyor. The drive to the screw is arranged at its input end whilst the output end is supported by a bearing 5b.

The helical pitch of the screw 4 increases along its length, gradually expanding from one equal to the bottle diameter at the input end to about 1.5 times this at the output end. Thus bottles enter the screw 4 from the main conveyor touching each other and are then smoothly accelerated during their passage along its length and emerge spaced at a pitch of 1.5 times the bottle diameter.

The moving conveyor 3 is driven from the screw 4 or by a second variable speed drive (not shown) which allows the conveyor velocity to be made equal to the velocity of the bottles emerging from the screw 4 irrespective of the setting of the first variable speed drive which determines the throughput of the machine. This arrangement also ensures that the spacing of the emergent bottles is maintained as they travel downstream through the inspection station 2 supported only by their bases resting on the conveyor 3. During this movement the bottles pass in turn through the inspection station, to be described later, and after inspection they are accepted by a second helical feed screw 7 which is supported by a bearing 8 at its input and is driven at its exit end from the first feed screw 4. The drive 5c is preferably such that the timing can be adjusted so that the entrance to the first pocket of the helical screw 7 is in the right place to accept bottles without disturbing their position on the moving conveyor 3. The crest of the helix at the entry point is tapered to facilitate this. Bottle guide rails 9a and 9b confine the bottles in the helices of the screws 4 and 7 respectively during their passage therethrough.

One purpose of this second screw 7 is to isolate the inspection zone from the effect of any back pressure from downstream bottles. It also provides a convenient location for a bottle rejection mechanism such as described in the specification of co-pending application Ser. No. 873,683, now U.S. Pat. No. 4,158,624 issued June 19, 1979, which requires that the bottle to be rejected is in a predetermined position downstream from the inspection station.

The method according to this invention of achieving complete inspection of the side walls of a bottle without rotating it is based on the fact that it has been found possible to see contaminating objects anywhere on the inside surface of the body of a bottle by viewing it from two directions substantially at right angles, in plan view. Both the near and far sides of the bottle surface can be seen from each of the two viewing directions.

To this end, in the embodiment illustrated in FIG. 1, the bottle 1f in the centre 6 of the inspection station 2 is illuminated in two directions at right angles by the lamps 10a, 10b, which may be tungsten filament lamps, fluorescent discharge lamps, Xenon flash tubes or any other source appropriate to the containers' colour or density. Light diffusing screens 11 are positioned in front of the respective lamps.

A lens 12 produces two images of the bottle side walls as viewed from the two directions 13 and 14 approximately at right angles. Two mirrors 15 and 16 and two further mirrors 17 and 18 enable a single lens 12 to produce the two images side-by-side on an integrated circuit device 19 comprising an array of photo-diodes arranged in a plurality of rows in combination with means to interrogate each diode in turn, along each row in turn. A suitable integrated circuit device having 64 rows each of 64 photo-diodes in a square format and known as "2DI 64×64 matrix array" is made by Integrated Photomatrix Limited of Dorchester, England.

A separator plate 20 in the image space of the lens prevents extraneous light outside the left hand image from degrading the right hand image and vice-versa.

Figure 2:
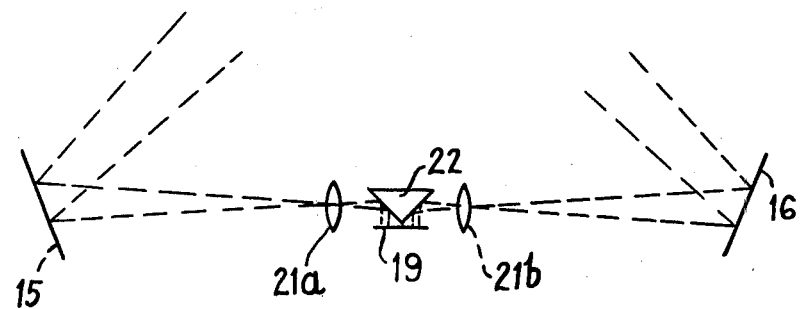
FIG. 2 is a fragmentary plan view of an alternative lens arrangement of the optical system of FIG. 1.

An alternative optical arrangement using separate lenses 21a, 21b for each viewing direction is shown in FIG. 2 where a 90° surface silvered mirror 22 in the image space of the two lenses reflects the two image forming light beams to produce the two bottle images side-by-side on the photo-diode array 19 as before.

Figure 3:
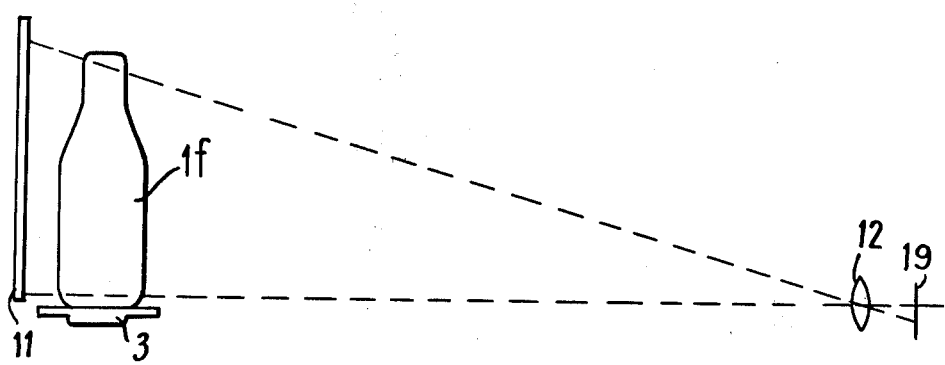
FIG. 3 is a schematic side view along one light path indicated by the line A—A of FIG. 1.

FIG. 3 is a side view along the viewing path A—A showing the bottle 1f in the centre 6 of the inspection station 2 and standing on the conveyor 3. The diagram represents just one of the two directions of view, the mirrors 16 and 18 being omitted for clarity. The light diffuser 11 illuminates the bottle 1f and the light rays are collected by the lens 12 and brought to a focus on the photo-diode array 19. The lens 12 is mounted at a level close to the plane on which the bottle is standing so that the near and far sides of the lowest part of the body of the bottle may be seen without obstruction from the bottle base or conveyor.

Figure 4:
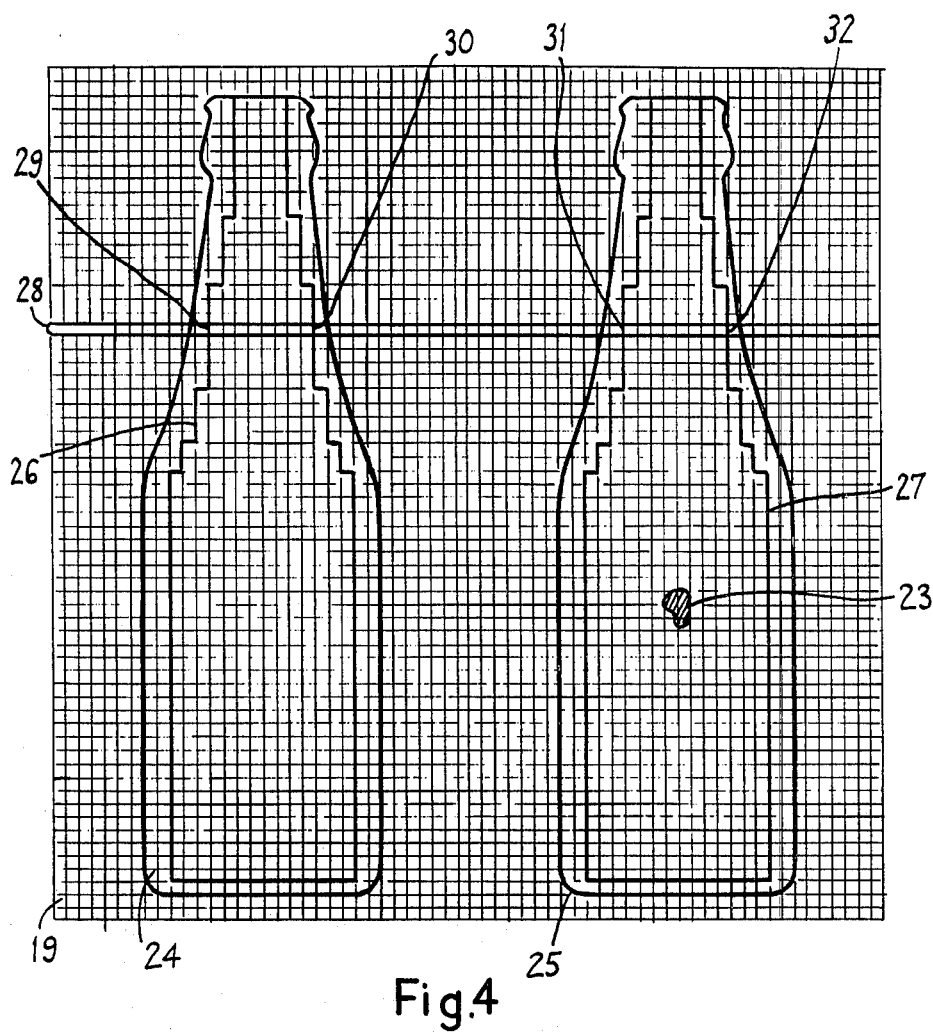
FIG. 4 shows the active surface of the integrated photodiode array with the two images of the side walls arranged side-by-side.

FIG. 4 shows the active surface of the array 19 with the two images 24, 25 side-by-side and a contaminating object 23 visible from one of the two directions of view.

The array is scanned horizontally line by line in sequence and produces a video signal whose amplitude at any instant is proportional to the light energy, integrated over the period between successive scans, which has been received by the photo-diode being scanned at that instant.

The array is scanned continuously and the video output is gated by a signal derived from one or more sensors arranged to detect the presence of a bottle at the inspection station. The time duration of this gating signal must be long enough for the whole of the array to be scanned. Scanning rates of 800 to 1000 frames per second are possible with this type of array, therefore, the gating time must be about 1.25 millisecs minimum. During this time a typical beverage bottle passing through the machine at a rate of 750 bottles per minute will have moved about 1 mm whilst being inspected and, therefore, the image blurr due to movement will be negligible.

The video signal derived from the bottle whilst it is in the inspection station is differentiated to obtain pulses which indicate a fast transition from light to dark or vice-versa along each of the scanned lines of the array. Such pulses indicate the presence of a foreign body and is used to activate a bottle reject device at the appropriate time.

Figure 5:
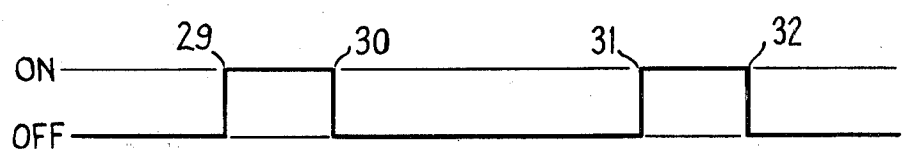
FIG. 5 shows the gating signal for one of the rows or lines of the photo-diode array.

FIG. 4 shows in detail the surface of the photo-diode array 19 on which the two images of the bottle 24, 25 as seen in two directions at right angles are focused and positioned side-by-side for simultaneous scanning by the array scanner. The areas of interest which together cover substantially the whole surface of the body of the bottle are defined by the boundary lines 26 and 27. A programmable read only memory device (PROM) is programmed to provide a further video gating signal which is used to accept reject signals derived from these two areas defined by the boundary lines 26, 27 and to ignore other signals from the rest of the array. For example, for line number 20 of the array, indicated at 28 in FIG. 4, the PROM is required to gate the video signal from this line ON after the 12th diode has been reached, OFF after the 20th diode, ON again after the 44th and OFF after the 52nd diode. These points are indicated at 29, 30, 31 and 32 respectively and the gating signal for this line is shown in FIG. 5.

The circuitry 50 for differentiating the video output, gating out unwanted signals from areas of the field outside that of interest, and for effecting the other operations described above is basically as described in the specification of copending application Ser. No. 930,167 and illustrated in FIG. 6 hereof.

Figure 6:
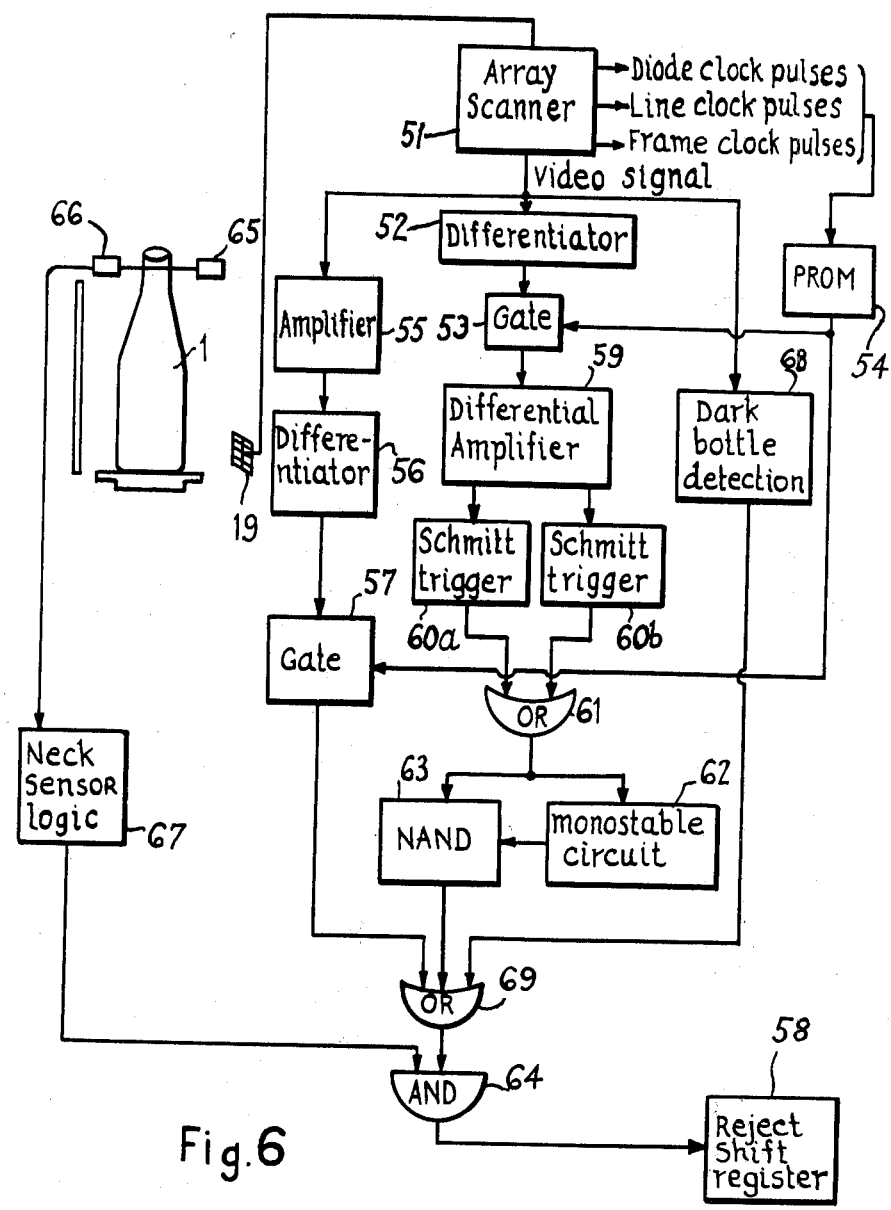
FIG. 6 is a circuit diagram.

As shown in FIG. 6, the photo-diode array 19 is scanned by an array scanner 51 to provide a video signal. This video signal is applied to a differentiator 52 the output from which is fed to a gate 53. The clock pulses of the array scanner 51 used to interrogate the array, diode by diode along a line, and line by line over the whole frame of the array, are used to address a programmable read only memory (PROM) 54 which is programmed to generate gating pulses of the correct ON-OFF gating periods for each line, as above explained. These gating pulses control the gating of gate 53, so that the only pulses which remain in the differentiated video output are those due to foreign bodies or dirt in the bottle.

The PROM may be programmed to define an area or areas of any shape within which desired signals may occur and outside which spurious signals must be rejected.

A large foreign body having straight edges aligned parallel to the lines scanned will not be detected because it would obscure all the active diodes in the line and, since there would be no change in illumination along the line, the differentiated output would be zero. To overcome this problem, a reject signal is also derived from the video signal comprising a whole frame which, before differentiating and gating, consists of 64 line signals. This signal is passed to an amplifier 55 having a restricted high frequency response so that the output cannot follow the fast change taking place between each line signal and a smoothed output results for each frame.

The two unwanted signals at the beginning and end of each frame may be gated out with a pulse generated in the PROM 54 and applied to a gating circuit 57 so that only the wanted signal remains and can be used together with any foreign body pulses on the line signals to send a reject pulse to the reject shift register 58 which operates some mechanism such as that described in U.S. Ser. No. 873,683, now U.S. Pat. No. 4,158,624 issued June 19, 1979, to divert the contaminated bottle from the bottle conveyor.

The two differentiators 52 and 56, one dealing with line signals and the other with the complete frame signal, both give outputs of either polarity depending on whether the illumination change is light to dark or vice-versa. With a small object both polarities will generally be present but a large object may generate signals of only one polarity depending on the direction of scan across the edge of the object.

It is convenient at some stage in the signal processing to invert signals of one polarity so that they are all the same. The differentiated signals obtained from foreign bodies in the bottle are pulses, approximately triangular in shape, but varying in amplitude and duration depending on the size and opacity of the body detected. A very small body which only obscures one diode in a line will be small in amplitude and of short duration compared with a body which obscures say ten consecutive diodes.

The differentiated signals may be used to drive a "Schmitt" trigger giving a constant amplitude output pulse for the length of time the input is above a preset threshold. This latter may be set to a low value so that even the signal from a single obscured diode will give an output from the trigger.

Separate "Schmitt" triggers 60a, 60b may be used on the positive and negative polarity parts of the signal which are amplified in the differential amplifier 59. The resulting pulses of the same polarity are combined in the "OR" gate 61.

The resulting pulse train provides the input to a monostable circuit 62 and also to a NAND gate 63. The monostable circuit 62 is made to give an output pulse of constant amplitude and time duration for each input pulse, the time duration being adjustable by altering the time constant of the Resistance-Capacitance coupling components. The output from the monostable circut 62 provides a second input to the NAND gate 63.

The NAND gate 63 will now only give an output when the signal pulse duration exceeds the preset pulse length of the monostable circuit 62. Thus the circuit performs as a pulse length comparitor and, by adjusting the time constant of the monostable circuit 62, all pulses of shorter duration than the present pulse length may be elminated from the NAND gate output which is fed to the reject shift register 56.

Thus, very small objects obscuring one diode can be detected or ignored by adjusting the time constant of the monostable circuit appropriately. Also a permanent spurious signal caused by the failure of one diode in the array may be ignored. The arrangement also gives a measure of immunity from very short duration interference pulses which may have been picked up by the earlier parts of the circuit.

In a practical bottle inspection machine it is necessary to be able to vary the sensitivity to different sized objects to avoid rejecting too many clean bottles with minor glass flaws or bottles carrying conveyor lubricant foam on the outside.

With the system described, the sensitivity may be varied as described or by adjusting the time constant of the differentiators or by varying the threshold at which the "Schmitt" triggers operate.

The diode array is continuously being scanned and delivers the video signal, which is processed in the manner described above. An AND gate 64 is provided in the output and is operated by a bottle position sensor 65 so that reject signals, if any, are only obtained when a bottle is in the inspection station.

The sensor is arranged to allow a bottle movement of 1 to 2 mm. before switching the output gate 64 off. Only reject signals obtained during this time reach the reject shift register 58.

The preferred method of sensing the bottle position employs a source 65 providing 2 to 3 narrow beams of infra red or visible light positioned so that they are interrupted by the mouth of a bottle passing through the inspection station. The spacing of the two outer beams in relation to the mouth diameter determines the distance the bottle travels during inspection. The photo-transistors (only one is shown at 66) which receive the two or three beams provide signals which operate logic devices 67 to perform other functions as well as that of gating the signals to the reject device, for example, they can be used to gauge the mouth diameter so that oversize or undersized bottles may be rejected.

Furthermore, logic may be provided so that inspection is only initiated when the bottle passes through the beams in the correct direction. This eliminates problems caused by a bottle possibly moving backwards a short distance.

Other detection systems can be incorporated with this inspection system and their respective reject signals can be fed into the system so that the same reject mechanism may be used for a number of purposes. For example, a sensor may be provided to detect water in the bottle being inspected. Also a dark bottle detector 68 controlled by the video signal or by a separate single photo-transistor arranged to view the bottle, may be provided to reject a bottle with totally obscured side walls or with a cork jammed in its neck. The output from the dark bottle detector 68 may be combined in the "OR" gate 69 with the outputs from the NAND gate 63 and from the gate 57.

In an alternative arrangement the output from the gate 57 may be fed into the differential amplifier 59.

We claim:

1. Apparatus for inspecting the side walls of transparent or translucent bottles for the detection of dirt or foreign bodies therein while the bottles are being conveyed to bottle filling apparatus, comprising a conveyor for moving the bottles to be inspected, supported only by their bases resting on the conveyor, through an inspection station, means for driving said conveyor continuously at a selected linear speed, means for delivering successive bottles to said conveyor in spaced apart relation and at a speed of movement equal to the linear speed of the conveyor, means for diffusely illuminating the side walls of a bottle as it moves through the inspection station, means for projecting, while a bottle is so illuminated, a plurality of images of the side walls of the bottle, as viewed from at least two different directions in plan, on to at least one integrated circuit device comprising an array of photo-diodes arranged in a plurality of rows with a plurality of diodes in each row in combination with array scanner means cyclically to scan the array and interrogate each diode in turn, along each row in turn, to provide a video signal comprising a sequence of electrical signals corresponding to the light energy each diode has received, means synchronised with said array scanner means to generate gating pulses of the desired length for each row, and means for feeding said video signal to electric circuit means including means for differentiating said video signal and gate means controlled by said gating pulses for gating-out unwanted signals outside the limits of the images of the side walls of the bottle to be inspected whereby to generate differentiated signal pulses representative of dirt or foreign bodies in the bottle, said electric circuit means also including means for inverting the differentiated signal pulses of one polarity so that all signal pulses are of the same polarity.

2. Apparatus as claimed in claim 1, wherein said projection means includes optical means mounted substantially level with the plane on which the base of the bottle is resting and producing two images of the side walls illuminated in said two directions and projecting said images onto said at least one integrated circuit device.

3. Apparatus as claimed in claim 1, wherein the interrogation of the photo-diodes of the integrated circuit device is controlled by clock pulses which are also used to address a programmable read only memory which is programmed to generate gating pulses of the desired length for each row, means feeding said video signal to a first differentiator, to a dark bottle detector and to an amplifier having a restricted high frequency response so that its output cannot follow the fast change in the video signal between the interrogation of successive rows of diodes, a first gate connected to the output of said first differentiator and controlled by said gating pulses to effect said gating-out of unwanted signals outside the limits of the side walls of the bottle to be inspected, the output from said first gate being fed to a differential amplifier the positive and negative outputs from which are fed to two "Schmitt" triggers respectively each producing a constant amplitude output pulse of the same polarity for the length of time the differentiated input pulse is above a preset threshold, a first "OR" gate combining the output pulses of said two "Schmitt" triggers and delivering the output pulses to a monostable circuit producing an output pulse of constant amplitude and time duration for each input pulse and also to a "NAND" gate, means for adjusting the time duration of the output pulses of said monostable circuit, means connecting the monostable circuit output to provide a second input to said "NAND" gate, a second differentiator connected to the output from said amplifier having a restricted high frequency response and having its differentiated output pulses fed to a second gate controlled by said gating pulses to effect gating-out of unwanted signals at the beginning and end of each output pulse corresponding to the interrogation of a whole frame consisting of all the successive whole rows of diodes, means connecting the outputs of said second gate, said "NAND" gate and said dark bottle detector to a second "OR" gate, a bottle position sensor for sensing when a bottle is in a position where it can be inspected, means connecting the outputs from said bottle position sensor and said second "OR" gate to an "AND" gate, and bottle reject control means connected to respond to the output from said "AND" gate.

4. Apparatus as claimed in claim 1, and including a mechanism which accelerates successive bottles during their approach to their point of delivery to said conveyor so that they are spaced apart when they arrive at said delivery point and are delivered on to the conveyor at the linear speed of the conveyor.

5. Apparatus as claimed in claim 4, and including mechanism which decelerates successive bottles leaving the inspection station to arrange them in substantially touching relationship.

6. Apparatus as claimed in claim 1, wherein the electric circuit means includes means for converting the differentiated signal pulses to constant amplitude pulses having a time duration corresponding to the length of time the differentiated pulse amplitude is above a preset threshold.

7. Apparatus as claimed in claim 6, and including means for varying said preset threshold.

* * * * *